(12) United States Patent
Broucek et al.

(10) Patent No.: US 12,274,994 B2
(45) Date of Patent: Apr. 15, 2025

(54) CHOLINE CHLORIDE COMPOSITIONS

(71) Applicant: Balchem Corporation, New Hampton, NY (US)

(72) Inventors: Reinhard Broucek, New Hampton, NY (US); Michael R. Sestrick, Warwick, NY (US)

(73) Assignee: BALCHEM CORPORATION, New Hampton, NY (US)

( * ) Notice: Subject to any disclaimer, the term of this patent is extended or adjusted under 35 U.S.C. 154(b) by 848 days.

(21) Appl. No.: 17/334,243

(22) Filed: May 28, 2021

(65) Prior Publication Data
US 2021/0370254 A1 Dec. 2, 2021

Related U.S. Application Data

(60) Provisional application No. 63/031,365, filed on May 28, 2020.

(51) Int. Cl.
| | | |
|---|---|---|
| *B01J 2/30* | (2006.01) | |
| *A23L 29/00* | (2016.01) | |
| *A23L 33/15* | (2016.01) | |
| *A23L 33/29* | (2016.01) | |
| *A23P 10/43* | (2016.01) | |

(52) U.S. Cl.
CPC .............. *B01J 2/30* (2013.01); *A23L 29/015* (2016.08); *A23L 33/15* (2016.08); *A23L 33/29* (2016.08); *A23P 10/43* (2016.08)

(58) Field of Classification Search
CPC ........... B01J 2/30; A23L 29/015; A23L 33/15; A23L 33/29; A23L 29/04; A23L 29/294; A23P 10/43; A23K 20/142; A23K 20/24; A61K 31/14; A61K 9/143; A61K 9/145; A61K 45/06; A23V 2002/00
See application file for complete search history.

(56) References Cited

U.S. PATENT DOCUMENTS

| | | | | |
|---|---|---|---|---|
| 2,623,901 | A | | 12/1952 | Klein et al. |
| 4,775,540 | A | * | 10/1988 | Hertel ..................... A23K 40/10 426/74 |
| 4,820,532 | A | * | 4/1989 | Bayer ..................... A61K 9/143 426/74 |
| 6,806,235 | B1 | | 10/2004 | Mueller et al. |
| 8,335,343 | B2 | | 12/2012 | Martiska et al. |
| 2005/0019413 | A1 | * | 1/2005 | Cavassini .............. A23K 20/28 514/642 |
| 2009/0214628 | A1 | | 8/2009 | De Rijk |
| 2010/0233320 | A1 | | 9/2010 | Sunvold et al. |
| 2016/0000070 | A1 | | 1/2016 | Mcknight et al. |

(Continued)

FOREIGN PATENT DOCUMENTS

| | | |
|---|---|---|
| EP | 2206440 A1 | 7/2010 |
| WO | 2016/007456 A1 | 1/2016 |
| WO | 2017/166565 A1 | 10/2017 |

OTHER PUBLICATIONS

International Search Report and Written Opinion for PCT/US2021/034846 dated Sep. 17, 2021, 14 pages.

(Continued)

*Primary Examiner* — Andrew J. Oyer
(74) *Attorney, Agent, or Firm* — BakerHostetler

(57) ABSTRACT

The present disclosure encompasses a non-caking, free-flowing composition comprising choline chloride.

26 Claims, 7 Drawing Sheets

(56) References Cited

U.S. PATENT DOCUMENTS

2016/0353775 A1* 12/2016 Dull .................. A23P 10/47
2017/0087199 A1   3/2017 Patron et al.
2019/0110510 A1* 4/2019 Altena .................. A23P 10/20

OTHER PUBLICATIONS

Anonymous: "Food Additives Ameliorating the Flavors, Enriching the Food", Food Additives World, Mar. 1, 2014 (Mar. 1, 2014), pp. 1-4, XP055911602, Retrieved from the Internet: URL: https://web.archive.org/web/20140316040122/http://www.foodadditivesworld.com:80/anticaking-agents.html [retrieved on Apr. 11, 2022].
Extended European Search Report for European Application No. 21812451.9, dated Mar. 20, 2024 (13 Pages).
Aristov et al., "Selective water sorbents for multiple applications, 1. CaCl2 confined in mesopores of silica gel: Sorption properties", React. Kinet. Catal. Lett., 1996, 59(2), 325-333.
Berghof Easy H2O, System for Chemical-Free Thermo-Coulometric Water Detection, Version 1.0 User Manual, 2004, 56 pages.
Berghof Easy H2O, System for Chemical-Free, Thermo-Coulometric Water Detection, Version 1.1 User Manual, 2004, 59 pages.
Caking Test, Revolution Powder Analyzer User Manual, Aug. 30, 2014, 10 pages.
Flowability Test, Revolution Powder Analyzer User Manual, Feb. 25, 2018, 48 pages.
Fluidization Test, Revolution Powder Analyzer User Manual, Aug. 30, 2014, 32 pages.
Granulation Test, Revolution Powder Analyzer User Manual, Aug. 30, 2014, 11 pages.
Mixing Test, Revolution Powder Analyzer User Manual, Aug. 30, 2014, 38 pages.
Packing Test, Revolution Powder Analyzer User Manual, Aug. 30, 2014, 37 pages.

* cited by examiner

- Anhydrous CaCl₂ works fast and has ample capacity to pickup moisture
- CaCl₂·2H₂O also works, but has lower capacity and slow water pickup
- TMC is inferior to CaCl₂·2H₂O at 15%RH
- Other additives tested did not work at 15%RH (test setup: weight increase of a small sample on a petri dish in the climate chamber set at 25°C, 15%RH)

CHOLINE CHLORIDE COMPOSITIONS

CROSS REFERENCE TO RELATED APPLICATIONS

This application claims priority to U.S. Provisional Application No. 63/031,365, filed May 28, 2020, the disclosure of which is incorporated herein by reference.

FIELD

The present disclosure encompasses a composition comprising choline chloride, wherein the composition is non-caking and free-flowing.

BACKGROUND

An important characteristic of powders and granular material is flowability—i.e., the ease with which a powder or a granular material will flow under a specified set of conditions. Many powders and granular materials tend to undergo an aggregation process known as caking. Caking may be manifested as severe formation of hard lumps or even complete solidification into a rock-hard mass. Caking adversely affects manufacturing processes, resulting in increased wear and tear on machines and possibly complete blockage of storage equipment or dosing units.

While exposure to high temperatures and/or humidity promotes caking for most powders and granular materials, for commercial choline chloride crystals (e.g., choline chloride as specified by the United States Pharmacopeia) caking problems occur even in closed, temperature-controlled packing. Because of the extreme hygroscopic nature of choline chloride, choline chloride particles readily cake and bridge together to form a solid mass in packaging, making the final product difficult or impossible to handle.

Accordingly, there remains a need in the art for choline chloride compositions that have improved handling, and methods of preparing the same.

SUMMARY OF THE DISCLOSURE

Described herein are non-caking and free-flowing compositions comprising choline chloride and at least one additive. Non-caking is defined herein as not performing moisture caking during storage in closed packaging under ambient temperature fluctuations, and free-flowing is characterized by a dynamic avalanche test resulting in one or more of the following parameter results: break energy lower than 170 kJ/kg, absolute break energy (ABS) lower than 300 kJ/kg, an avalanche angle lower than 50°, broadness of break energy distribution (defined as standard deviation over repeated avalanches) of <50% of the parameter value, or broadness of break energy ABS distribution, defined as standard deviation over repeated avalanches, of <20% of the parameter value. The composition has a free moisture value of below 0.5%. The choline chloride may be USP compliant before the at least one additive is added. The composition may be used in combination with a mineral or vitamin premix.

The at least one additive of the disclosed composition may include a lubricant. In some examples the lubricant may be magnesium stearate, calcium stearate, or fumed silica, in an amount from about 0.5-5% by weight.

The at least one additive of the disclosed composition may be a humectant. In some aspects, the humectant may have the ability to take up at least 5% water at 25° C., at 15% relative humidity, within 15 hours. In some examples, the humectant may include calcium chloride dihydrate in an amount from about 0.5-5% by weight, wherein the calcium chloride dihydrate has a moisture content of less than or equal to 2%. In some additional examples, the humectant may include calcium chloride anhydrous.

The composition may further comprise a hydrophobic compound that reduces or slows the deliquescence behavior of the composition at ambient conditions. In some examples, the hydrophobic compound is magnesium stearate or calcium stearate. In some other examples, the hydrophobic compound is a diglyceride.

Also described herein are methods of making the composition described above. The method may include adding a humectant to USP grade choline chloride crystals, wherein the humectant has the ability to take up at least 5% water at 25° C., at 15% relative humidity, within 15 hours. In some examples of the method, no drying is needed after the humectant is added to the crystals. The method may also include adding a hydrophobic compound.

Another method of making the composition is disclosed herein, which includes combining an additive to USP grade choline chloride crystals and mixing the combination while drying the combination. This method may also include adding a humectant, wherein the humectant has the ability to take up at least 5% water at 25° C., at 15% relative humidity, within 15 hours.

DETAILED DESCRIPTION

Figure 1:
FIG. 1 depicts photographs of sample A and B on a roller shaker.

The present disclosure provides a composition comprising choline chloride, where the choline chloride is suitable for human and animal applications, and where the composition is non-caking and free-flowing in closed packaging. In certain embodiments, where the composition is intended for human consumption, the choline chloride may be compliant with the United States Pharmacopoeia (USP). The USP criteria specify that no additives may be used in the crystallization step of choline chloride, and residual moisture of the choline chloride may not exceed 0.5% wt. Additional aspects of the invention include processes for making such choline chloride compositions.

I. Compositions Comprising Choline Chloride

The present disclosure provides compositions comprising choline chloride crystals, where the composition is non-caking and free-flowing in closed packaging. In certain embodiments, the crystals meet the United State Pharmacopeia (USP) criteria for choline chloride crystals suitable for human applications, while simultaneously being non-caking and free-flowing in closed packaging. As used herein, the phrase "USP criteria" refers to choline chloride as specified by the United States Pharmacopoeia $43^{rd}$ Revision (USP43). USP-grade choline chloride contains no less than 99.0% and no more than 100.5% of choline chloride, calculated on the anhydrous basis, and no more than 0.5% water. Additional requirements for USP-grade choline chloride, as well as analytic tests for determining amount of choline chloride, water, impurities, etc., are set forth in the USP 43.

Compositions of the present disclosure, in addition to choline chloride, may contain one or more additives. Such additives are detailed below.

(a) Choline Chloride Crystals

Generally speaking, choline chloride crystals are manufactured by first forming choline chloride via a chemical reaction performed in water, then removing the water to form the crystalline product. The chemical reaction that forms choline chloride is typically accomplished by reacting ethylene oxide and trimethylamine hydrochloride or epichlorohydrin, in water. The water in the reaction mixture can be removed directly to form solid choline chloride, or alternately the water can be removed in a two-step process. Direct removal of the water may be performed by any means known in the art, including but not limited to heat and/or vacuum. In the two-step process, the reaction mixture is first concentrated until crystals of choline chloride are formed (e.g. the wet cake). Then the wet cake is dried. Drying can typically involve mixing the wet cake, heating the wet cake, applying a vacuum to the wet cake, or any combination of mixing, heating, or applying a vacuum. For instance, by way of non-limiting example, the wet cake may be mixed, heated, and subject to a vacuum to remove moisture, the wet cake may be mixed, and heated to remove moisture, or the wet cake may be only mixed to remove moisture. Alternatively, any method known in the art to dry a choline chloride wet cake may be employed to dry the wet cake. Methods for mixing, heating, and applying vacuum pressure to a mixture are known in the art, and are described in more detail in the Examples below.

(b) Additives

A composition of the present disclosure, in addition to choline chloride, comprises one or more additives. These additives enable the composition to be non-caking and free-flowing in closed packaging. Generally speaking, an additive may be added at the wet cake stage of manufacturing choline chloride, after the choline chloride has been fully dried, or while the choline chloride is dried. If an additive is added after drying, it is minimally mixed with the composition, and such mixing may additionally involve heating or vacuum pressure.

In some embodiments, a composition of the present disclosure may comprise an additive that is a humectant. A suitable humectant is one that can be used in human applications, and that can keep the ambient moisture of a choline chloride composition below the critical humidity of choline chloride crystals in closed packaging. More specifically, a suitable humectant has the ability to take up at least 5% water at 25° C., at 15% relative humidity, within 15 hrs. In preferred embodiments, a suitable humectant has the ability to take up at least 5, 10, 15, 20, or 25% water at 25° C., at 15% relative humidity within 15 hrs. In particular embodiments, a suitable humectant has the ability to take up at least 5% water at 25° C., at 15% relative humidity, within 10 hours. Non-limiting examples of suitable humectants include anhydrous calcium chloride and calcium chloride dihydrate ($CaCl_2 \cdot 2H_2O$). Examples of non-suitable humectants include trimesoyl chloride.

A suitable humectant may be added to the wet cake of choline chloride, may be added after the wet cake has been dried, or may be added while the wet cake is being dried. Generally speaking, if a humectant is added to the wet cake of choline chloride, then the drying step comprises more than mixing. For instance, the drying step may comprise heating, vacuum pressure, or a combination thereof. If a humectant is added after the wet cake has been dried, then in some embodiments the mixture may be merely mixed to form a composition of the present disclosure, or in other embodiments, the mixture may be heated or exposed to vacuum pressure to form a composition of the present disclosure.

In particular embodiments, if the humectant is anhydrous calcium chloride or calcium chloride dihydrate, then the humectant may be added to the wet cake and the mixture may be dried using mixing, heating, and vacuum pressure to form a composition of the present disclosure. In certain embodiments, if the humectant is anhydrous calcium chloride or calcium chloride dihydrate, then the humectant may be added after drying, and the resulting mixture may be merely mixed, or mixed with heat to form a composition of the present disclosure.

Additives other than humectants may also be used. For instance, some additives may be added during or after drying of choline chloride manufacturing such that the mixing of the choline chloride with the additive facilitates the removal of residual moisture and can be useful for altering the particle properties of the final product. In preferred embodiments, an additive may have lubricating properties.

Suitable additives may include lubricants. Non-limiting examples of lubricants may include stearates and silicas. For example, magnesium stearate or calcium stearate may be used as suitable lubricants. In certain embodiments, a suitable lubricant may include a stearate that is a partial glyceride. Silicas, such as fumed silicas, may also be used as lubricants.

Compositions of the present disclosure may also comprise more than one additive. For instance, a composition may comprise both a humectant and an additive that isn't a humectant. Alternatively, a composition may comprise a single additive that behaves as both a humectant and as a lubricant. Suitable examples of such a mixed additive include selective water sorbants, such as calcium chloride adsorbed on the inner surface of fumed silica.

Compositions of the present disclosure may comprise from about 0.2 wt % to about 6 wt % of an additive (whether two components or as a single component). For instance, a composition of the present disclosure may comprise about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 wt % of an additive. In some embodiments, a composition of the present disclosure may comprise from about 0.5% to about 5% of an additive, by weight. Generally speaking, the amount of additive required in a composition of the present disclosure will depend on the residual moisture of the choline chloride crystals and the moisture uptake capacity of the additive (e.g. if the additive is a humectant).

(c) Caking

Choline chloride compositions of the present disclosure do not exhibit significant caking and retain this attribute after storage under suitable conditions. Stated another way, compositions comprising choline chloride of the present disclosure do not substantially cake upon storage in closed packaging under ambient temperature fluctuations. Caking describes a composition's tendency to agglomerate, compact, and/or form physical bridges between particles while those particles are resting (i.e., not moving). Caking can lead to the formation of rock-hard chunks during storage.

Suitable storage conditions include storage in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liner inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g. laminates of aluminum foil with polyolefins, polyesters, styrenics or copolymers thereof). In an aspect, a composition comprising choline chloride of the present disclosure may be stored in moisture resistant packaging at room temperature. It is noted that room temperature encompasses storage in non-environmentally controlled conditions, such as trucking containers, rail containers, or warehouses. In another aspect, choline chloride compositions of the present disclosure may be stored in moisture resistant packaging at temperatures ranging from about 15° C. to about 30° C. In yet another aspect, choline chloride compositions of the present disclosure may be stored in moisture resistant packaging at temperatures ranging from about 20° C. to about 25° C. In some aspects, choline chloride compositions of the present disclosure may be stored in moisture resistant packaging at about 15° C., about 16° C., about 17° C., about 18° C., about 19° C., about 20° C., about 21° C. about 22° C., about 23° C., about 24° C., about 25° C., about 26° C., about 27° C., about 28° C., about 29° C., or about 30° C. In another aspect, a composition comprising choline chloride of the present disclosure may be stored in moisture resistant packaging at temperatures ranging from about 20° C. to about 25° C. In some aspects, a composition comprising choline chloride of the present disclosure may be stored in moisture resistant packaging at about 20° C., about 21° C. about 22° C., about 23° C., about 24° C., or about 25° C.

In various embodiments, a composition comprising choline chloride of the present disclosure does not substantially cake after no less than about 2 years of storage under the conditions described in this section. In still other embodiments, a composition comprising choline chloride of the present disclosure does not substantially cake after no less than about 1 year of storage under the conditions described in this section. In certain embodiments, a composition comprising choline chloride of the present disclosure does not substantially cake after no less than about 12 months, 11 months, 10 months, 9 months, 8 months, 7 months, 6 months, 5 months, 4 months, 3 months, 2 months, or 1 month of storage under the conditions described in this section.

(d) Free-Flowing

A choline chloride composition of the present invention is free-flowing under suitable storage conditions. Generally speaking, the phrase "free-flowing" refers to the behavior of a composition once in motion. A choline chloride composition of the present invention is free-flowing if it is characterized by a dynamic avalanche test resulting in one or more of the following parameter results: (a) break energy lower than 170 kJ/kg, (b) absolute break energy (ABS) lower than 300 kJ/kg, (c) an avalanche angle lower than 50°, (d) broadness of break energy distribution, defined as standard deviation over repeated avalanches, of <50% of the parameter value, or (e) broadness of ABS distribution, defined as standard deviation over repeated avalanches, of <20% of the parameter value. Dynamic avalanche testing is known in the art. Generally speaking, the test uses a drum filled with the sample, which rotates to test the flowability of the product. The drum rotates at 20 rpm and produces 150 avalanches per measurement. Immediately in front of the drum, a camera is positioned to record each avalanche, and then computers are used to determine several parameters that are related to flowability. Among these, the absolute break energy, break energy and the avalanche angle are the most representative.

Absolute break energy (ABS energy) represents the maximum energy level of the sample powder before an avalanche begins. It is detected as a peak in the potential energy of the powder over the time sequence of images recorded by the camera. The potential energy of the powder is given by the following equation:

$$E = mgh$$

where E is potential energy in J, m is mass in kg, g is acceleration due to gravity (9.8 m/s$^2$), and h is height in meters.

This potential energy level represents the amount of energy required to start each avalanche. The reported ABS energy is the average break energy for all of the powder avalanches made.

The break energy is the maximum potential energy of the sample before an avalanche begins minus the lowest potential energy level the powder sample can have.

The graphical representation of both break energy and ABS break energy is a distribution over the number of avalanches made (final output is represented as a histogram). The smaller the standard deviation is, the narrower the energy break and energy break ABS distribution is over the number of avalanches made.

The avalanche angle represents the maximum angle from horizontal reached by the powder before an avalanche occurs during the rotation. This measurement is the average value for all the avalanche angles. Methods of performing dynamic avalanche testing is known in the art, and may be performed, for instance, using a REVOLUTION Powder Analyzer® manufactured by Mercury Scientific Inc.

Suitable storage conditions include storage in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liner inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g.

laminates of aluminum foil with polyolefins, polyesters, styrenics or copolymers thereof). In an aspect, a composition comprising choline chloride of the present disclosure may be stored in moisture resistant packaging at room temperature. It is noted that room temperature encompasses storage in non-environmentally controlled conditions, such as trucking containers, rail containers, or warehouses. In another aspect, choline chloride compositions of the present disclosure may be stored in moisture resistant packaging at temperatures ranging from about 15° C. to about 30° C. In yet another aspect, choline chloride compositions of the present disclosure may be stored in moisture resistant packaging at temperatures ranging from about 20° C. to about 25° C. In some aspects, choline chloride compositions of the present disclosure may be stored in moisture resistant packaging at about 15° C., about 16° C., about 17° C., about 18° C., about 19° C., about 20° C., about 21° C. about 22° C., about 23° C., about 24° C., about 25° C., about 26° C., about 27° C., about 28° C., about 29° C., or about 30° C. In another aspect, a composition comprising choline chloride of the present disclosure may be stored in moisture resistant packaging at temperatures ranging from about 20° C. to about 25° C. In some aspects, a composition comprising choline chloride of the present disclosure may be stored in moisture resistant packaging at about 20° C., about 21° C. about 22° C., about 23° C., about 24° C., or about 25° C.

In various embodiments, a composition comprising choline chloride of the present disclosure remains free-flowing after no less than about 2 years of storage under the conditions described in this section. In still other embodiments, a composition comprising choline chloride of the present disclosure remains free-flowing after no less than about 1 year of storage under the conditions described in this section. In certain embodiments, a composition comprising choline chloride of the present disclosure remains free-flowing after no less than about 12 months, 11 months, 10 months, 9 months, 8 months, 7 months, 6 months, 5 months, 4 months, 3 months, 2 months, or 1 month of storage under the conditions described in this section.

(e) Water Content

In another aspect, a composition comprising choline chloride of the present disclosure contains no more than 0.5% water. Stated another way, the total water content is less than or equal to 0.5%. Preferably, the total water content is about 0.3% or less, more preferably about 0.25% or less, even more preferably about 0.2% or less. In certain embodiments, the total water content is about 0.2% or less. In other embodiments, the total water content is about 0.15% or less. In still other embodiments, the total water content is about 0.1% or less. Total water content may be determined by Method I<921> USP 39, including Method 1a (Direct Titration), Method 1b (Residual Titration), and Method 1c (Coulometric Titration). In an exemplary method, total water content is determined by high-temperature coulometric detection of water, for example, using a Berghof EasH$_2$O® instrument.

In some embodiments, a composition comprising choline chloride of the present disclosure contains no more than 0.5% water after no less than about 12 months, 11 months, 10 months, 9 months, 8 months, 7 months, 6 months, 5 months, 4 months, 3 months, 2 months, or 1 month of storage in moisture resistant packaging at temperatures ranging from about 15° C. to about 30° C., or about 20° C. to about 25° C.

In some embodiments, a composition comprising choline chloride of the present disclosure contains no more than 0.5% water after no less than about 24 months, 21 months, 18 months, 15 months, or 12 months of storage in moisture resistant packaging at temperatures ranging from about 15° C. to about 30° C., or about 20° C. to about 25° C.

In some embodiments, a composition comprising choline chloride of the present disclosure contains no more than 0.5% water after no less than about 12 months, 11 months, 10 months, 9 months, 8 months, 7 months, 6 months, 5 months, 4 months, 3 months, 2 months, or 1 month of storage in moisture resistant packaging at temperatures ranging from about 25° C. to about 40° C. with 75% relative humidity.

(f) Storage Ability

In some aspects, a composition comprising choline chloride of the present disclosure has improved storage ability. As used herein, "storage ability" refers to the ability of a material to resist caking for a prolonged period of time. In various embodiments, a composition comprising choline chloride of the present disclosure may have storage ability of at least about 1 month. In an aspect, the storage ability of a composition comprising choline chloride of the present disclosure may be from about 1 month to about 2.5 years, about 1 month to about 2 years, about 1 month to about 1.5 years, about 1 month to about 1 year, about 1 month to about 6 months, or about 1 month to about 3 months. In other embodiments, a composition comprising choline chloride of the present disclosure may have storage ability of at least about 1 month in room temperature. In an aspect, the storage ability of a composition comprising choline chloride of the present disclosure may be from about 1 month to about 3 years, about 1 month to about 2.5 years, about 1 month to about 2 years, about 1 month to about 1.5 years, about 1 month to about 1 year, about 1 month to about 6 months, or about 1 month to about 3 months in room temperature. In still other embodiments, a composition comprising choline chloride of the present disclosure may have storage ability of at least about 1 month in moisture resistant packaging. Formats of moisture resistant packaging/containers may include, but are not limited to, multi-walled paper bags having a suitable moisture barrier, including aluminum, or fiber drums having polymeric or aluminum foil linings integral with the drum wall or loose liners inserts. Rigid containers such as blow molded drums and pails made of polymers with moisture barriers may also be used. The container may be a flexible package such as a shipping bag made of a polymer substrate. In one embodiment, the packaging may be made from aluminum foil laminated to polymer films formed from polymers that are commonly used to make moisture resistant packaging (e.g. laminates of aluminum foil with polyolefins, polyesters, styrenics or copolymers thereof). In an aspect, the storage ability of a composition comprising choline chloride of the present disclosure may be from about 1 month to about 2.5 years, about 1 month to about 2 years, about 1 month to about 1.5 years, about 1 month to about 1 year, about 1 month to about 6 months, or about 1 month to about 3 months when stored in moisture resistant packaging.

(g) Combinations

The present disclosure also encompasses combinations of a choline chloride composition of the present invention and other compositions suitable for human or animal use. For instance, by way of non-limiting example, a choline chloride composition of the present invention may be combined with a vitamin or mineral premix, a nutraceutical, a food item, or an animal feed or supplement.

II. Methods of Preparing a Choline Chloride Composition Described Herein

A method of making a composition of the present disclosure generally comprises crystallizing choline chloride as described in section I above, using methods commonly known in the art, and then combining the crystals with at least one additive. As detailed above, suitable additives may be mixed with the choline chloride at step 2 of the manufacturing process (e.g. the wet cake), after step 3 of the manufacturing process (e.g. after drying the wet cake), or during step 3 of the manufacturing process (e.g. while drying the wet cake).

Methods of mixing one or more additives with the choline chloride are known in the art, as well as methods of drying the mixture of choline chloride with one or more additives.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

261 g commercial choline chloride crystals (USP-grade, about 0.3% moisture) were mixed and further dried on a ROTAVAP (Büchi) under vacuum at 60° C. for 4 h. The sample was then sieved in dry atmosphere (<20% RH) through a 1.4 mm sieve and divided into 2 equal parts (A and B). Part A was stored in a glass bottle (Schott). To part B (121.16 g), 1.5% (1.82 g) $CaCl_2 \cdot 2H_2O$ were added. The sample was put back on the ROTAVAP and mixed further under vacuum at 60° C. for about 3 h.

Caking of samples A and B of example 1 were compared by the following tests:

Visual Inspection in Glass Bottle:

Sample A lumped after a few days. Sample B could be shaken up, even after 4 years of storage FIG. 1 shows the behavior of the samples on a roller shaker.

Caking Test Under Pressure:

The system consists of a tube (3.4 cm inner diameter), which can be taken apart. About 20 g of sample are put in the tube, which is closed with a movable piston. On top of the piston a weight of 165 g/cm² was applied. The setup was put in a glove box (manufactured by Sicco (www.sicco.de)) and kept below 20% RH at ambient temperature.

Figures 2A, 2B:
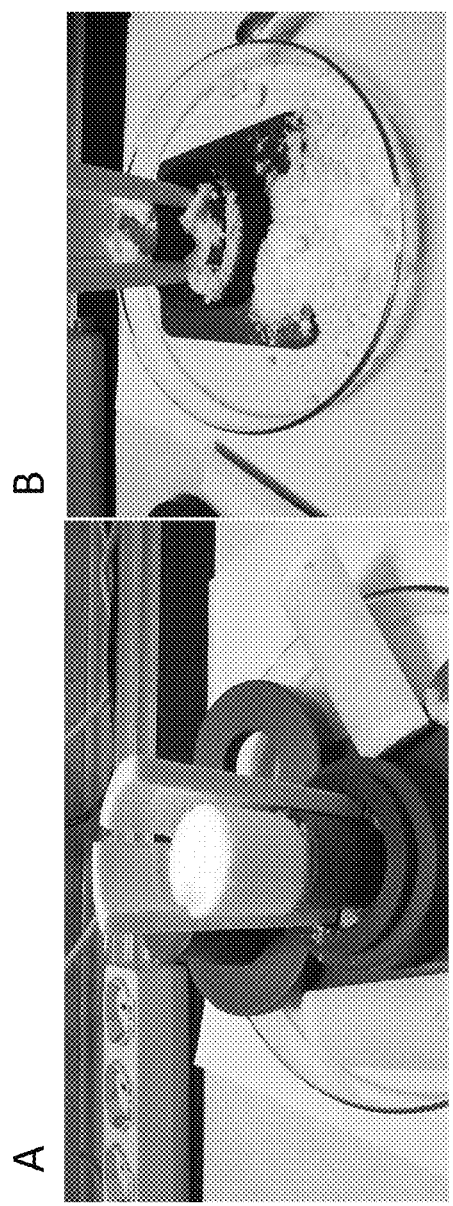
FIG. 2A depicts a photograph illustrating that sample A formed a solid cylinder.
FIG. 2B depicts a photograph illustrating that sample B, with $CaCl_2$), crumbled upon slight touching.

After 1 week, the tube was disassembled and the product inspected. Sample A, without additive, formed a solid cylinder (FIG. 2A), sample B, with $CaCl_2$), crumbled on slight touching (see FIG. 2B).

Examples 2-7

The following setup was used in examples 2-7:

A 2 L lab mixer/dryer (IKA Magic plant), equipped with an upward pumping spiral stirrer and a temperature/pressure sensor, with the jacket heated by a thermostat (Huber). The setup was connected to a vacuum pump (VACUUBRAND) and a nitrogen-source for purging the headspace. Stirrer speed and torque were controlled by the IKA-software; the rest of the setup was controlled by a process control system (HiTec-Zang).

Example 2 ($CaCl_2 \cdot 2H_2O$)

352 g of commercial choline chloride crystals (USP-grade, <0.2% moisture) were put in the mixer/dryer, the jacket temperature set to 70° C. After 25 min, 5.28 g $CaCl_2 \cdot 2H_2O$ (Sigma, 1.5 w % on input) were added. The vessel was closed and the vacuum turned on (about 10 mbar). The stirring under vacuum was continued for 3 h during which the jacket temperature was increased in 2 steps to 80° C. After cooling down to room temperature, the bottom outlet was opened and the product flew out without further help (yield 99.7%).

The product was stored in a glass bottle and kept its dry and free-flowing aspect over time (a minimum of 19 months).

The analysis with the REVOLUTION-tester (Mercury Scientific) gave:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 85.2 | 8.5 | 267 | 8 | 42.5 |

Example 3 (MgSt)

301.25 g of commercial choline chloride crystals (USP-grade, <0.2% moisture) were put in the mixer/dryer. The jacket temperature was first set to 60° C. and vacuum applied. After 45 min the jacket temperature was increased to 75° C. After 75 min the vacuum was released and 4.52 g magnesium stearate (MgSt) (FACI, 1.5 w % on input) were added. The vessel was closed and the vacuum turned on again. The stirring under vacuum was continued for about 4 h during which the jacket temperature was increased in 5 degrees steps to 90° C. After cooling down to room temperature, the bottom outlet was opened and the product flew out without further help (yield 99.2%).

The product was stored in a glass bottle and kept its dry and free-flowing aspect over time (a minimum of 14 months).

The analysis with the REVOLUTION-tester (Mercury Scientific) gave:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 40.03 | 3.8 | 209 | 4 | 35.1 |

Example 4 (CaSt)

343.77 g of commercial choline chloride crystals (USP-grade, <0.2% moisture) were put in the mixer/dryer. The jacket temperature was first set to 60° C. and vacuum applied. After 45 min the jacket temperature was increased to 75° C. After 75 min the vacuum was released and 5.16 g calcium stearate (CaSt) (FACI, 1.5 w % on input) were added. The vessel was closed and the vacuum turned on again. The stirring under vacuum was continued for about 4 h during which the jacket temperature was increased in 5 degrees steps to 90° C. After cooling down to room temperature, the bottom outlet was opened and the product flew out without further help (yield 97%).

The product was stored in a glass bottle and kept its dry and free-flowing aspect over time (a minimum of 13 months).

The analysis with the REVOLUTION-tester (Mercury Scientific) gave:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 50.9 | 2.8 | 219.2 | 2.6 | 36 |

Example 5 (silica)

243.93 g of commercial choline chloride crystals (USP-grade, <0.2% moisture) were put in the mixer/dryer like in example 2. The jacket temperature was first set to 60° C. and vacuum applied. After 45 min the jacket temperature was increased to 75° C. After 75 min the vacuum was released and 5.16 g silica (SIPERNAT 33, EVONIK, 1.5 w % on input) were added. The vessel was closed and the vacuum turned on again. The stirring under vacuum was continued for about 4 h during which the jacket temperature was increased in steps to 85° C. As the torque of the mixer increased at this level, the jacket temperature was reduced to 75° C. After cooling down to room temperature, the bottom outlet was opened and the product flew out without further help (yield 99.4%).

The product was stored in a glass bottle and kept its dry and free-flowing aspect over time (a minimum of 14 months).

The analysis with the REVOLUTION-tester (Mercury Scientific) gave:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 57.8 | 3.8 | 237.1 | 3.3 | 38.6 |

Example 6 (TMC, Counterexample)

375 g of commercial choline chloride crystals (USP-grade, <0.2% moisture) were put in the mixer/dryer like in example 2. The jacket temperature was first set to 60° C., then increased to 70° C. and vacuum applied. After 45 min the jacket temperature was increased to 75° C. After 90 min the vacuum was released and 5.63 g silica (TMC, JUNGBUNZLAUER, 1.5 w % on input) were added. The vessel was closed and the vacuum turned on again. The stirring under vacuum was continued for about 3 h during which the jacket temperature was increased in steps to 80° C. As the torque of the mixer increased at this level, the jacket temperature was reduced to 75° C. After cooling down to room temperature, the bottom outlet was opened and the product flew out without further help (yield 100%).

The product was stored in a glass bottle. It did not stay free-flowing as the analysis with the REVOLUTION-tester (Mercury Scientific) showed (done next day):

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 173.4 | 87.1 | 316.5 | 90.8 | 83.7 |

Example 7 (Talc, Counterexample)

360.33 g of commercial choline chloride crystals (USP-grade, <0.2% moisture) were put in the mixer/dryer like in example 2. The jacket temperature was first set to 60° C. and vacuum applied. After 45 min the jacket temperature was increased to 75° C. After 20 min at this temperature the vacuum was released and 5.4 g talc (E553, Mineral Imesco, 1.5 w % on input) were added. The vessel was closed and the vacuum turned on again. The stirring under vacuum was continued for about 3 h during which the jacket temperature was increased in steps to 85° C. As the torque of the mixer increased at this level, the jacket temperature was reduced to 75° C. After cooling down to room temperature, the bottom outlet was opened and the product flew out without further help (yield 99.8%).

The product was stored in a glass bottle. It did not stay free-flowing, as the analysis with the REVOLUTION-tester (Mercury Scientific) showed (done next day):

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 185.1 | 97.8 | 362.9 | 83.9 | 56.7 |

It is believed that this is because the choline chloride absorbed water faster than talc.

Example 8

Example 8 provides evidence of an additive having a high enough water binding capacity and fast sorption kinetics to absorb all free moisture of the product without the need of simultaneous drying as in examples 1-7.

Dried $CaCl_2$ works well for this purpose (removing at least 1 crystal water from the dihydrate by standard drying, vacuum and/or heat, is needed to start the effect).

Figure 3:
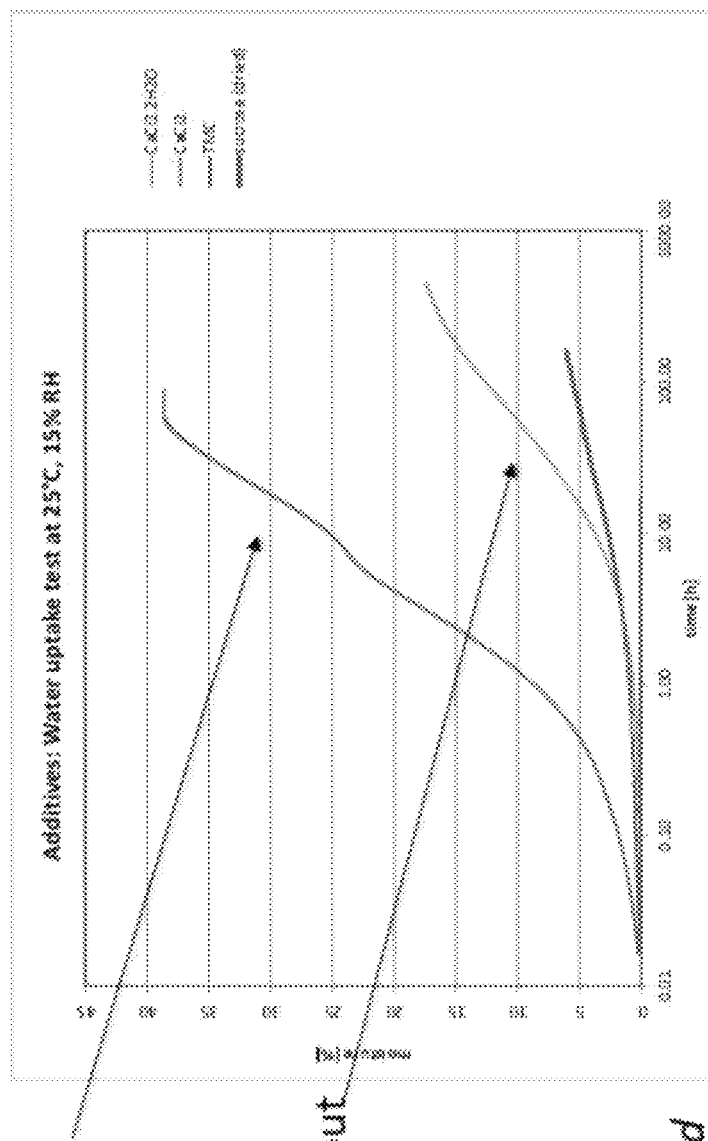
FIG. 3 is a diagram that shows the humidity absorption characteristic needed for a suitable humectant; TMC and other humectants, which do not display the sorption characteristics needed, failed in mixing tests under ambient conditions.

The diagram of FIG. 3 shows the humidity absorption characteristic needed to achieve this effect; $CaCl_2 \cdot 2H_2O$, TMC and other humectants, which do not display the sorption characteristics needed, failed in mixing tests under ambient conditions.

195.87 g of commercial choline chloride crystals (USP-grade, <0.2% moisture) were put in the mixer/dryer, the jacket temperature set to 25° C. After 5 min, 2.22 g $CaCl_2$ (Sigma, dried in vacuum stove, equivalent to 1.5 w % $CaCl_2 \cdot 2H_2O$ on input) were added. The vessel was closed, no vacuum applied and the temperature not increased. The stirring was continued for 1 h, then the bottom outlet was opened and the product flew out without further help (yield 99.3%). The product was stored in a glass bottle and kept its dry and free-flowing aspect over time (a minimum of 14 months).

The analysis with the REVOLUTION-tester (Mercury Scientific) gave:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 77.6 | 5.1 | 256.2 | 4.9 | 38.2 |

Example 9 ($CaCl_2 \cdot 2H_2O$)

Example 9 is a counterexample which shows that $CaCl_2 \cdot 2H_2O$ cannot absorb/reduce the free residual moisture of the CC-crystals just with ambient mixing. The same setup as in examples 2-7 was used.

295.53 g of commercial choline chloride crystals (USP-grade, <0.2% moisture) were put in the mixer/dryer, the jacket temperature set to 25° C. After 5 min, 4.43 g $CaCl_2 \cdot 2H_2O$ (Sigma, 1.5 w % on input) were added. The vessel was closed, no vacuum applied and the temperature not increased. The stirring was continued for 1 h, then the bottom outlet was opened. The product did not flow out freely, opening the vessel it was evident that the fluffy, snowflake-like aspect of fine, additive-free CC-crystals did not change by mixing in $CaCl_2 \cdot 2H_2O$ under ambient conditions. As the product was not flowing, no analysis with the REVOLUTION-tester was made.

Examples 10-11

Examples 10 and 11 are examples demonstrating a combination of additives to fine tune or improve the properties of non-caking/free-flowing choline chloride crystals (CC-crystals).

Example 10

Combining $CaCl_2$) with a hydrophobic second additive, e.g. stearates or diglycerides improves the deliquescent behavior of the product.

Figure 4:
FIG. 4 depicts photographs showing that at ambient conditions (25° C., 50% RH) choline chloride crystals are deliquescent in a short time, e.g. a small sample of choline chloride crystals plus $CaCl_2$) is dissolved completely within 5 min.
Figure 4:
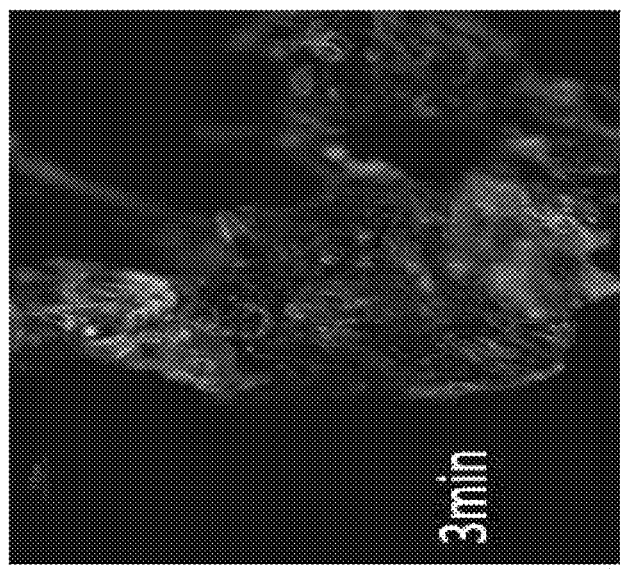
Figure 4:
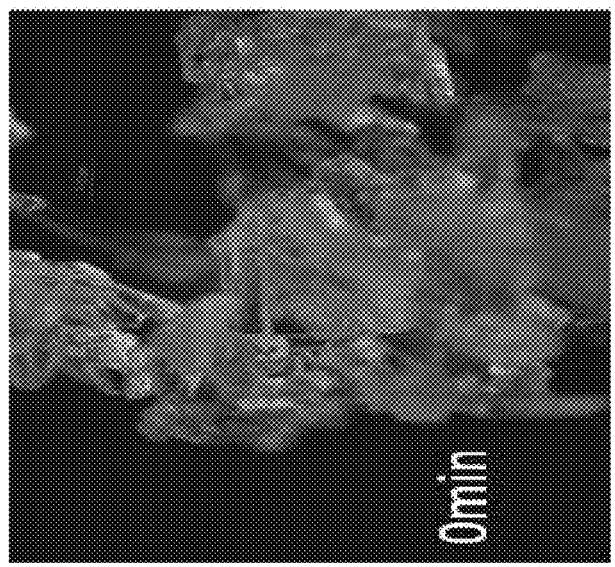

At ambient conditions (25° C., 50% RH) CC-crystals are deliquescent in short time, e.g. a small sample of CC-crystals plus $CaCl_2$) is dissolved completely within 5 min (see FIG. 4).

Figure 5:
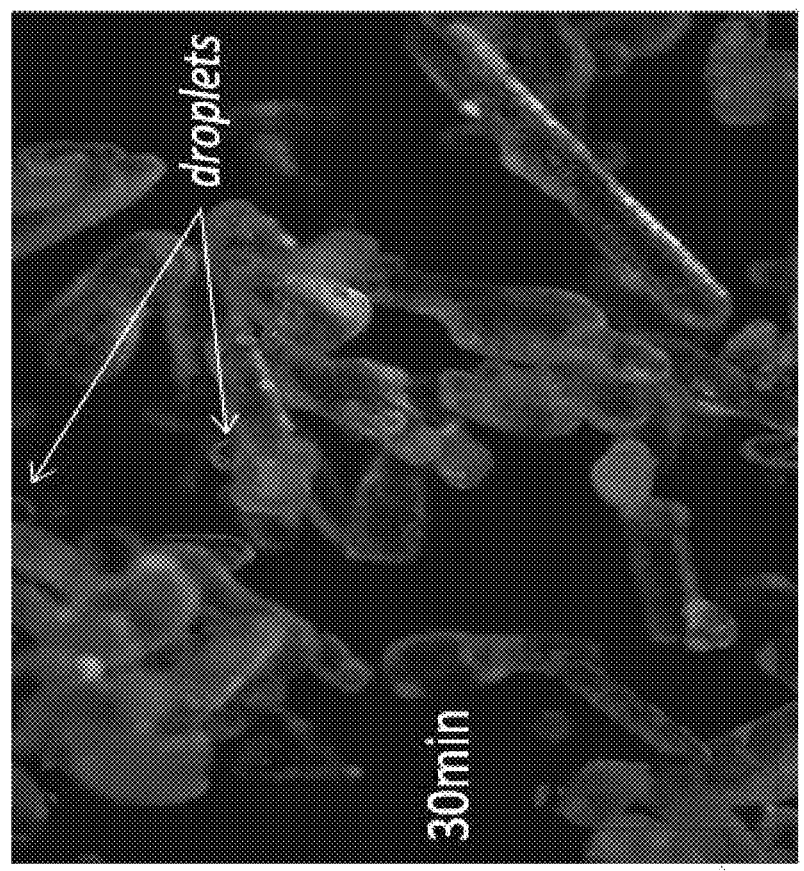
FIG. 5 depicts photographs showing that the hygroscopicity of the product when combined with a hydrophobic compound is not greatly impacted, but the moisture attracted stays outside of the crystals.
Figure 5:
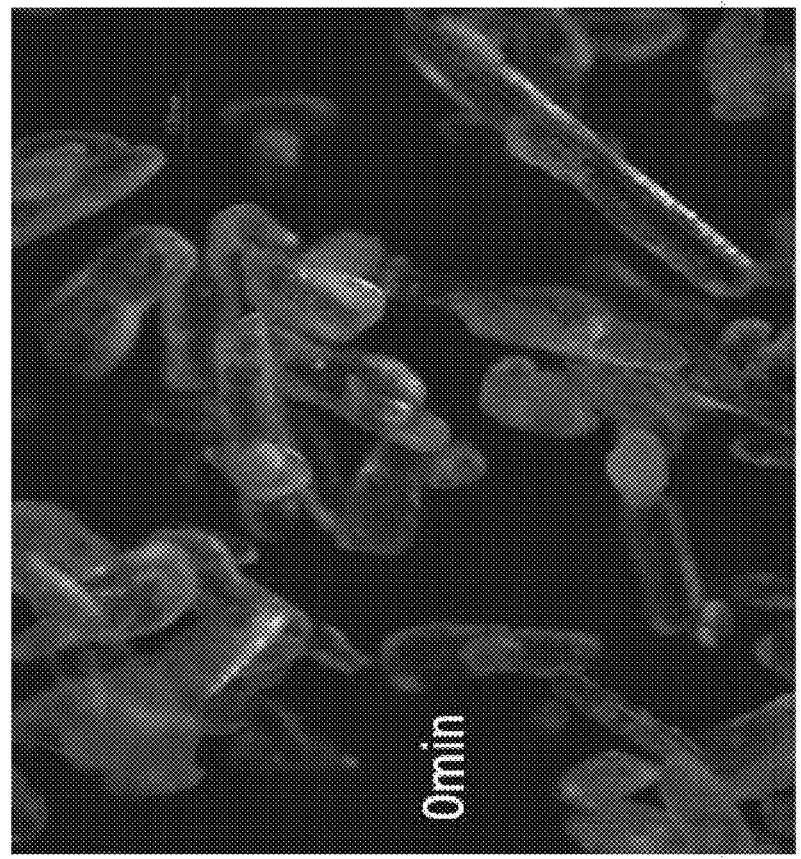

Adding a diglyceride (9% Precirol ATO 5, Gattefossé) to these CC-crystals keeps the particle structure intact, the deliquescense is therefore much reduced by combining $CaCl_2$) with a hydrophobic additive (see FIG. 5). FIG. 5 shows that the hygroscopicity of the product is not reduced much, but the moisture attracted stays outside of the crystals.

Figure 6:
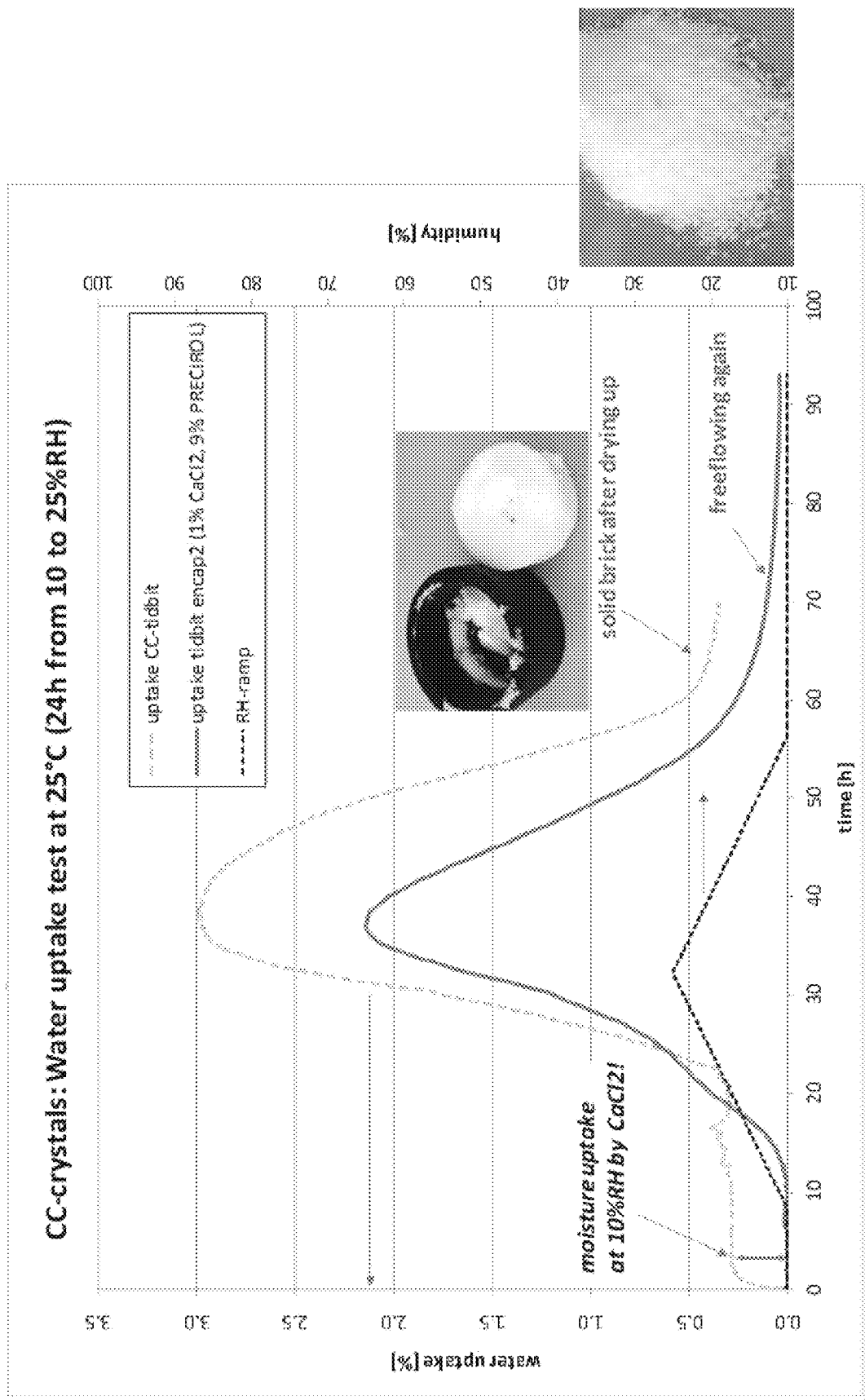
FIG. 6 is a graph depicting water uptake of choline chloride crystals at 25 C (24 h from 10 to 25% RH).

A simple moisture uptake/release-test elucidates the action of a hydrophobic additive further. A sample of the product is put in a Petri dish in a climate chamber set to 25° C. and 15% RH. A humidity ramp up to 25% RH was run in 24 h and then back again to 15% RH, also in 24 h. Weight gain and loss during the operation is registered by an analytical balance and the sample state after the whole tests investigated (see FIG. 6). It is evident that the $2^{nd}$, hydrophobic additive reduces the hygroscopicity and eliminates the deliquescense of the product.

Example 11

$CaCl_2$) can also be combined with silica to improve its sorption characteristics. This effect is known (see, for instance, Aristov et al. (1996) React. Kinet. Catal. Lett. 59(2):325-333, where the effect is described as "selective water sorbents" (SWS)).

Figure 7:
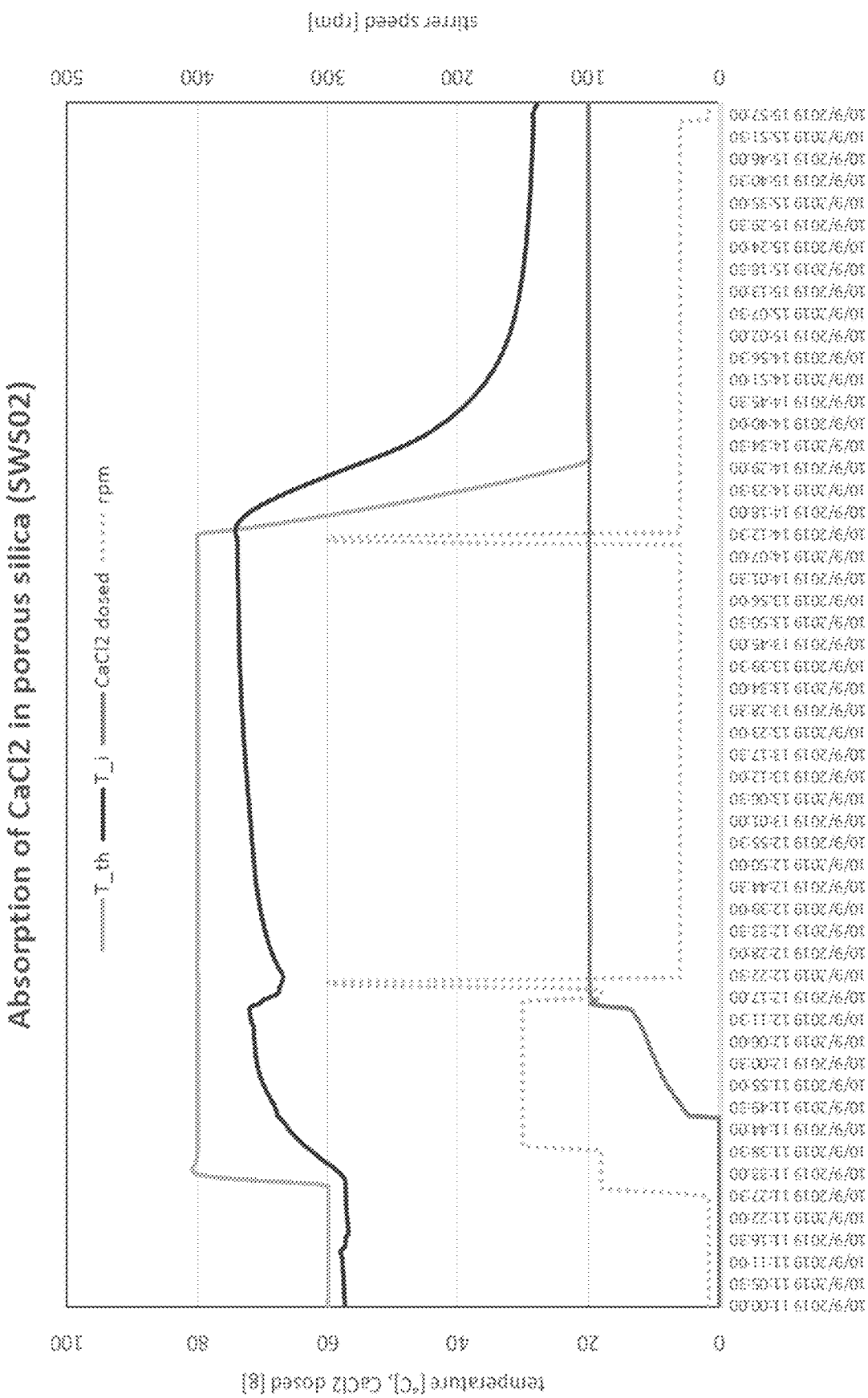
FIG. 7 is a graph depicting the absorption of $CaCl_2$) in porous silica.

A SWS was made in an 1 L-glass-reactor (Buechi) by adsorbing about 20 g of a 40% $CaCl_2 \cdot 2H_2O$ solution in water on 10.1 g silica (SIPERNAT 33, Evonik). The dosing must be adapted to the evaporation speed of the water, in this case the jacket of the dryer was heated to 60° C. (after 30 min increased to 80° C.), full vacuum applied and the $CaCl_2$)-solution absorbed and dried in about 4 h. At the end, the powder was as free-flowing as the silica used as starting material (see FIG. 7).

The SWS made this way was then mixed with commercial CC-crystals in the 1 L-Buchi-glass-reactor. The jacket was heated to 60° C. and 2% of SWS were slowly added to 114.13 g CC-crystals and mixed for 30 min under vacuum. The sample was cooled down to ambient temperature and bottled.

The product stayed non-caking and free-flowing in the closed glass bottle, the flowability test in the REVOLUTION-tester gave the following results:

| Break Energy (kJ/kg) | Break Energy SD (kJ/kg) | Break Energy Abs (kJ/kg) | Break Energy Abs SD (kJ/kg) | Avalanche Angle (deg) |
|---|---|---|---|---|
| 45.9 | 2.7 | 245.7 | 2.6 | 35.9. |

What is claimed is:

1. A composition comprising choline chloride and about 0.2% to about 6% by weight of the composition of calcium chloride, wherein the composition does not perform moisture caking during storage in closed packing under ambient temperature fluctuations, and wherein the composition is characterized by a dynamic avalanche test resulting in one or more of the following parameter results:
   (a) break energy lower than 170 kJ/kg,
   (6) absolute break energy (ABS) lower than 300 kJ/kg,
   (c) an avalanche angle lower than 50°,
   (d) broadness of break energy distribution, defined as standard deviation over repeated avalanches, of <50% of the parameter value, or
   (e) broadness of break energy ABS distribution, defined as standard deviation over repeated avalanches, of <20% of the parameter value.

2. The composition of claim 1, wherein the composition has a free moisture value below 0.5%.

3. The composition of claim 2, wherein the calcium chloride is adsorbed on the inner surface of fumed silica.

4. The composition of claim 2, having a free moisture value below 0.5% after 12 months of storage in moisture resistant packaging.

5. The composition of claim 1, further comprising a lubricant.

6. The composition of claim 5, wherein the lubricant is magnesium stearate or calcium stearate, in an amount from about 0.5-5% by weight of the composition.

7. The composition of claim 5, wherein the lubricant is a partial glyceride, in an amount from about 0.5-5% by weight of the composition.

8. The composition of claim 5, wherein the lubricant is fumed silica, in an amount from about 0.5-5% by weight by weight of the composition.

9. The composition of claim 1, comprising calcium chloride in an amount of from about 0.5-5% by weight of the composition.

10. The composition of claim 1, wherein the calcium chloride comprises calcium chloride dihydrate.

11. The composition of claim 1, wherein the calcium chloride has a moisture content of less than or equal to 2%.

12. The composition of claim 1, wherein the choline chloride is USP compliant before the calcium chloride is added.

13. The composition of claim 1, wherein the composition further comprises a hydrophobic compound that reduces or slows the deliquescence behavior of the composition at ambient conditions.

14. The composition of claim 13, wherein the hydrophobic compound is magnesium stearate or calcium stearate.

15. The composition of claim 13, wherein the hydrophobic compound is a diglyceride.

16. A combination, comprising the composition of claim 1, and a mineral or vitamin premix.

17. The composition of claim 1, wherein the calcium chloride comprises anhydrous calcium chloride.

18. The composition of claim 1, wherein the calcium chloride comprises up to 5 wt % of water.

19. The composition of claim 1, wherein the calcium chloride comprises up to 0.3 wt % of water.

20. The composition of claim 1, wherein the calcium chloride comprises up to 0.25 wt % of water.

21. The composition of claim 1, comprising calcium chloride in an amount of from about 0.5 to 2%, by weight of the composition.

22. A method of making a composition of claim 1, the method comprising mixing calcium chloride having a moisture content of less than or equal to 2% with USP grade choline chloride crystals.

23. The method of claim 22, wherein the calcium chloride has the ability to take up at least 5% water at 25° C., at 15% relative humidity, within 15 hrs.

24. The method of claim 22, where no drying is needed after the calcium chloride is added to the choline chloride crystals.

25. The method of claim 22, further comprising adding a hydrophobic compound to the composition.

26. The method of claim 22, further comprising drying the composition.

* * * * *